(12) United States Patent
Schwarz (10) Patent No.: US 8,211,455 B2
(45) Date of Patent: *Jul. 3, 2012

(54) IMPLANTABLE OR INSERTABLE MEDICAL DEVICES FOR CONTROLLED DELIVERY OF A THERAPEUTIC AGENT

(75) Inventor: Marlene C. Schwarz, Auburndale, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 774 days.

This patent is subject to a terminal disclaimer.

(21) Appl. No.: 10/175,136

(22) Filed: Jun. 19, 2002

(65) Prior Publication Data

US 2003/0236514 A1 Dec. 25, 2003

(51) Int. Cl.
*A61F 13/00* (2006.01)

(52) U.S. Cl. .................. 424/422; 424/423; 424/426

(58) Field of Classification Search .................. 424/422, 424/423, 436
See application file for complete search history.

(56) References Cited

U.S. PATENT DOCUMENTS

| | | | | |
|---|---|---|---|---|
| 4,341,889 A * | 7/1982 | Deichert et al. | ............... | 528/26 |
| 4,946,899 A | 8/1990 | Kennedy et al. | ............... | 525/244 |
| 5,019,096 A * | 5/1991 | Fox et al. | ............... | 600/36 |
| 5,061,276 A * | 10/1991 | Tu et al. | ............... | 623/1.33 |
| 5,258,020 A | 11/1993 | Froix | ............... | 623/1 |
| 5,304,121 A | 4/1994 | Sahatjian | ............... | 604/53 |
| 5,607,463 A * | 3/1997 | Schwartz et al. | ............... | 623/1.44 |
| 5,616,608 A | 4/1997 | Kinsella et al. | ............... | 514/449 |
| 5,716,981 A | 2/1998 | Hunter et al. | ............... | 514/449 |
| 5,733,925 A | 3/1998 | Kunz et al. | ............... | 514/449 |
| 5,741,331 A | 4/1998 | Pinchuk | ............... | 623/11 |
| 5,756,145 A * | 5/1998 | Darouiche | ............... | 427/2.24 |
| 5,879,697 A | 3/1999 | Ding et al. | ............... | 424/422 |
| 5,902,631 A * | 5/1999 | Wang et al. | ............... | 427/2.1 |
| 5,954,706 A | 9/1999 | Sahatjian | ............... | 604/509 |
| 6,054,504 A * | 4/2000 | Dalla Riva Toma | ............... | 523/122 |
| 6,099,562 A | 8/2000 | Ding et al. | ............... | 623/1.46 |
| 6,214,901 B1 * | 4/2001 | Chudzik et al. | ............... | 523/113 |
| 6,280,411 B1 | 8/2001 | Lennox | ............... | 604/103.05 |
| 6,306,166 B1 * | 10/2001 | Barry et al. | ............... | 623/1.46 |
| 6,306,419 B1 * | 10/2001 | Vachon et al. | ............... | 424/422 |
| 6,335,029 B1 | 1/2002 | Kamath et al. | ............... | 424/423 |
| 6,416,546 B1 * | 7/2002 | Kimura et al. | ............... | 623/1.46 |
| 6,527,938 B2 * | 3/2003 | Bales et al. | ............... | 205/229 |
| 6,558,686 B1 * | 5/2003 | Darouiche | ............... | 424/423 |
| 6,558,809 B1 * | 5/2003 | Kelch et al. | ............... | 428/520 |
| 6,630,215 B1 * | 10/2003 | Oda et al. | ............... | 428/35.7 |
| 2002/0016574 A1 | 2/2002 | Wang et al. | | |
| 2002/0107330 A1 | 8/2002 | Pinchuk et al. | ............... | 525/242 |
| 2004/0175406 A1 * | 9/2004 | Schwarz | ............... | 424/423 |

FOREIGN PATENT DOCUMENTS

| | | |
|---|---|---|
| EP | 0 166 998 A2 * | 1/1986 |
| EP | 0166998 | 1/1986 |
| EP | 0328421 A2 | 8/1989 |
| WO | WO 98/56312 | 12/1998 |
| WO | WO 98/56312 A1 * | 12/1998 |
| WO | WO 00/21584 | 4/2000 |
| WO | WO 00/62830 | 10/2000 |
| WO | WO 02/43788 A2 | 6/2002 |

OTHER PUBLICATIONS

Odian Principles of Polymerization 3rd ed., 1991, John Wiley and Sons, p. 142.*
O. Perez-Camacho et al., "Preparation of Hydroxyl-Functionalized SEBS for in Situ Graft Reaction Compatibilizing Agents," *Journal of Applied Polymer Science*, 64(13): 2519-2528 (1997).
Gantrez. Polymethyl vinyl ether/maleic anhydride copolymers, http://www.isp-pharma.com/library/gantrez/index.html; ISP Reference Guide for Pharmaceuticals: Gantrex, http://www.isp-pharma.com/library/gantrez/gantrez.html.

\* cited by examiner

*Primary Examiner* — James Rogers
(74) *Attorney, Agent, or Firm* — Mayer & Williams PC; David B. Bonham; Keum J. Park (57) ABSTRACT

The present invention is directed to novel implantable or insertable medical devices that provide controlled release of a therapeutic agent. According to an embodiment of the present invention, a therapeutic-agent-releasing medical device is provided, which comprises: (a) an implantable or insertable medical device; (b) a release layer disposed over at least a portion of the implantable or insertable medical device; and (c) a therapeutic agent. The release layer comprises a maleic anhydride polymer selected from (i) a maleic anhydride copolymer and (ii) a maleic anhydride graft polymer. The release layer regulates the rate of release of the therapeutic agent from the medical device upon implantation or insertion of the device into a patient. The present invention is also directed to methods of forming the above implantable or insertable medical devices, methods of administering a therapeutic agent to a patient using such devices, and methods of modulating the release of therapeutic agent from such devices.

44 Claims, 7 Drawing Sheets

IMPLANTABLE OR INSERTABLE MEDICAL DEVICES FOR CONTROLLED DELIVERY OF A THERAPEUTIC AGENT

FIELD OF THE INVENTION

The present invention relates to implantable or insertable medical devices for controlled delivery of one or more therapeutic agents.

BACKGROUND OF THE INVENTION

Numerous medical devices have been developed for the delivery of therapeutic agents to the body.

In accordance with some delivery strategies, a therapeutic agent is provided (a) within a polymeric carrier layer and/or (b) beneath a polymeric barrier layer that is associated with an implantable or insertable medical device. Once the medical device is placed at the desired location within a patient, the therapeutic agent is released from the medical device at a rate that is dependent upon the nature of the polymeric carrier and/or barrier layer.

The desired release profile for the therapeutic agent is dependent upon the particular treatment at hand, including the specific condition being treated, the specific therapeutic agent selected, the specific site of administration, and so forth. As a result, there is a continuing need for polymeric layers, including polymeric barrier layers and carrier layers, which are able to provide a broad range of therapeutic agent release rates.

SUMMARY OF THE INVENTION

The present invention is directed to novel implantable or insertable medical devices, which provide controlled release of a therapeutic agent.

According to a first aspect of the present invention, a therapeutic-agent-releasing medical device is provided, which comprises: (a) an implantable or insertable medical device; (b) a release layer disposed over at least a portion of the implantable or insertable medical device; and (c) a therapeutic agent. The release layer comprises a maleic anhydride polymer selected from (i) a maleic anhydride copolymer and (ii) a maleic anhydride graft polymer. The release layer regulates the rate of release of the therapeutic agent from the medical device upon implantation or insertion of the device into a patient.

In some embodiments, the release layer is a carrier layer that comprises the therapeutic agent. In other embodiments, the release layer is a barrier layer disposed over a therapeutic-agent-containing region, which comprises the therapeutic agent.

Preferred medical devices include catheters, guide wires, balloons, filters, stents, stent grafts, vascular grafts, vascular patches, shunts, and intraluminal paving systems. The device can be adapted, for example, for implantation or insertion into the coronary vasculature, peripheral vascular system, esophagus, trachea, colon, biliary tract, urinary tract, prostate or brain.

Beneficial therapeutic agents for the practice of the present invention include anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, and agents that interfere with endogenous vasoactive mechanisms.

Preferred maleic anhydride copolymers include copolymers comprising (a) a monomer comprising a carbon-carbon double bond and (b) a maleic anhydride monomer in a form selected from the anhydride form, free acid form, acid salt form and partial ester form. Monomers comprising a carbon-carbon double bond include alkylene monomers (e.g., ethylenes, propylenes and isobutylenes), vinyl monomers (e.g., vinyl aromatics, vinyl ethers, vinyl acetates, vinyl aliphatics, halogenated vinyl compounds, vinyl pyrrolidones, acrylonitriles, vinyl alcohols, and vinyl acrylamides), and acrylate monomers or derivatives of the same (e.g., methyl acrylates, methyl methacrylates, acrylic acids, methacrylic acids, hydroxyethyl acrylates, hydroxyethyl methacrylates, glyceryl acrylates, glyceryl methacrylates, acrylamides, methacrylamides and ethacrylamides).

Preferred, maleic anhydride copolymers for the practice of the present invention include random, alternating, graft and block copolymers.

Specific maleic anhydride copolymers for the practice of the present invention include: (a) alternating copolymers of isobutylene and maleic anhydride, (b) random copolymers of styrene and maleic anhydride, (c) alternating copolymer of styrene and maleic anhydride. (d) copolymers of styrene and maleic anhydride in which a first portion of the maleic anhydride is in the carboxyl or partial ester form and a second portion of the maleic anhydride is in the anhydride form, and (e) alternating copolymers of methyl vinyl ether and maleic anhydride.

Preferred maleic anhydride graft polymers include maleic anhydride graft polymers in which maleic anhydride is grafted onto a copolymer containing (a) one or more blocks of polystyrene and (b) one or more polymer blocks of ethylene and butylene.

In many preferred embodiments, the release layer will further comprise an additional polymer that is not a maleic anhydride polymer. In some of these embodiments, the additional polymer is blended with the maleic anhydride polymer in the release layer. In others, the additional polymer is crosslinked with the maleic anhydride polymer in the release layer. Specific examples of additional polymers for the practice of the present invention include (1) copolymers containing (a) one or more blocks of polyisobutylene and (b) one or more blocks of polystyrene or poly alpha-methylstyrene, (2) copolymers containing (a) one or more blocks of polystyrene and (b) one or more polymer blocks of ethylene and butylenes, and (3) poly(butyl methacrylates).

According to another aspect of the present invention, a method of making a therapeutic-agent-releasing medical device is provided. The method comprises: (a) providing a solution comprising one or more solvents and a maleic anhydride polymer selected from (i) a maleic anhydride copolymer and (ii) a maleic anhydride graft polymer; (b) applying the solution to a surface of an implantable or insertable medical device; and (c) removing the solvents from the solution to form a release layer. In many preferred embodiments, the solution further comprises an additional polymer that is not a maleic anhydride polymer. Solvent spraying is one preferred technique for applying the above solution.

In some embodiments (for example, where a carrier layer is being formed), the solution further comprises the therapeutic agent. In other embodiments (for example, where a barrier layer is being formed), the solution is applied over a therapeutic-agent-containing region that comprises the therapeutic agent.

According to another aspect of the present invention, a method of modulating a rate of release of a therapeutic agent from a release layer is provided. The release layer is disposed over at least a portion of an implantable or insertable medical device and comprises (i) a maleic anhydride polymer selected from a maleic anhydride copolymer and a maleic anhydride graft polymer and (ii) an additional polymer that is not a maleic anhydride polymer. Release is modulated by changing the composition of the release layer.

In some embodiments, the release rate can be modulated by changing the amount of the maleic anhydride polymer relative to the amount of the additional polymer. For example, the rate of release of the therapeutic agent can be increased in certain embodiments by increasing the amount of the maleic anhydride polymer relative to the amount of the additional polymer, while the rate of release can be decreased by decreasing the amount of the maleic anhydride polymer relative to the amount of the additional polymer.

In other embodiments, the release rate can be modulated by changing the amount of maleic anhydride monomer relative to the amount of the other monomers in the copolymer. For example, the rate of release of the therapeutic agent can be increased in certain embodiments by increasing the amount of maleic anhydride monomer relative to the other monomers, while the rate of release of the therapeutic agent can be decreased by decreasing the amount of maleic anhydride monomer.

In still other embodiments, the release rate can be modulated by changing the molecular weight of the maleic anhydride polymer. For example, the rate of release of the therapeutic agent can be increased in certain embodiments by decreasing the molecular weight of maleic anhydride polymer, while the rate of release can be decreased by increasing the molecular weight of the maleic anhydride polymer.

One advantage of the present invention is that implantable or insertable medical devices are provided, which provide for controlled release of a therapeutic agent.

Another advantage of the present invention is that implantable or insertable medical devices are provided, which are able to provide therapeutic agent release over a wide variety of time frames.

Another advantage of the present invention is that effective strategies are provided for controlling the release profile of a therapeutic agent from an implantable or insertable medical device.

These and other embodiments and advantages of the present invention will become immediately apparent to those of ordinary skill in the art upon review of the Detailed Description and Claims to follow.

DETAILED DESCRIPTION OF THE INVENTION

The present invention relates to the use of maleic anhydride copolymers and graft polymers in release layers that control the release of one or more therapeutic agents from an implantable or insertable medical device.

By "release layer" is meant a layer that regulates the rate of release of a therapeutic agent. Two preferred release layers for use in accordance with the present invention are carrier layers and barrier layers.

By "carrier layer" is meant a layer which contains at least one therapeutic agent and from which the therapeutic agent is released.

By "barrier layer" is meant a layer which is disposed between a source of therapeutic agent and a site of intended release and which controls the rate at which the therapeutic agent is released.

According to one aspect of the present invention, a medical device is provided which comprises an outer carrier layer disposed over at least a portion of an implantable or insertable medical device. The outer carrier layer comprises at least one maleic anhydride copolymer or graft polymer and a therapeutic agent. Upon implantation or insertion of the device, the therapeutic agent is released from the carrier layer in a controlled fashion.

According to another aspect of the present invention, an implantable or insertable medical device is provided, which comprises (a) a therapeutic-agent-containing region and (b) a barrier layer comprising a maleic anhydride copolymer or graft polymer disposed over the therapeutic-agent-containing region. Because the barrier layer is disposed over the therapeutic-agent-containing region, the barrier layer acts to control release of the therapeutic agent from the medical device after implantation or insertion of the same.

Preferred implantable or insertable medical devices for use in conjunction with the present invention include catheters (for example, renal or vascular catheters such as balloon catheters), guide wires, balloons, filters (e.g., vena cava filters), stents (including coronary vascular stents, cerebral, urethral, ureteral, biliary, tracheal, gastrointestinal and esophageal stents), stent grafts, cerebral aneurysm filler coils (including GDC—Guglilmi detachable coils—and metal coils), vascular grafts, myocardial plugs, patches, pacemakers and pacemaker leads, heart valves, biopsy devices, or any coated substrate (which can comprise, for example, glass, metal, polymer, ceramic and combinations thereof) that is implanted or inserted into the body, either for procedural use or as an implant, and from which therapeutic agent is released.

The medical devices contemplated for use in connection with the present invention include drug delivery medical devices that are used for either systemic treatment or for the localized treatment of any mammalian tissue or organ. Non-limiting examples are tumors; organs including but not limited to the heart, coronary and peripheral vascular system (referred to overall as "the vasculature"), lungs, trachea, esophagus, brain, liver, kidney, bladder, urethra and ureters, eye, intestines, stomach, pancreas, ovary, and prostate; skeletal muscle; smooth muscle; breast; cartilage; and bone.

One particularly preferred medical device for use in connection with the present invention is a vascular stent, which delivers therapeutic agent into the vasculature for the treatment of restenosis. As used herein, "treatment" refers to the prevention of a disease or condition, the reduction or elimination of symptoms associated with a disease or condition, or the substantial or complete elimination a disease or condition. Preferred subjects are mammalian subjects and more preferably human subjects.

"Therapeutic agents", "pharmaceutically active agents", "pharmaceutically active materials", "drugs" and other related terms may be used interchangeably herein and include genetic therapeutic agents, non-genetic therapeutic agents and cells. Therapeutic agents may be used singly or in combination.

Exemplary non-genetic therapeutic agents for use in connection with the present invention include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promoters; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; and (o) agents that interfere with endogenous vascoactive mechanisms.

Exemplary genetic therapeutic agents for use in connection with the present invention include anti-sense DNA and RNA as well as DNA coding for: (a) anti-sense RNA, (b) tRNA or rRNA to replace defective or deficient endogenous molecules, (c) angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include (a) plasmids, (b) viral vectors such as adenovirus, adenoassociated virus and lentivirus, and (c) non-viral vectors such as lipids, liposomes and cationic lipids.

Cells for use in connection with the present invention include cells of human origin (autologous or allogeneic), including stem cells, or from an animal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis. Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs(6-mercaptopurine), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Numerous additional therapeutic agents useful for the practice of the present invention are also disclosed in U.S. Pat. No. 5,733,925 assigned to NeoRx Corporation, the entire disclosure of which is incorporated by reference.

A wide range of therapeutic agent loadings can be used in connection with the medical devices of the present invention, with the amount of loading being readily determined by those of ordinary skill in the art and ultimately depending, for example, upon the condition to be treated, the nature of the therapeutic agent itself, the means by which the therapeutic agent is administered to the intended subject, and so forth.

The present invention utilizes release layers comprising maleic anhydride copolymers and graft polymers.

A "maleic anhydride copolymer" is a polymer formed from two or more dissimilar monomers, at least one of which is maleic anhydride or a maleic anhydride derivative, for example, the free acid, salt, or partial ester form of maleic anhydride. Such copolymers may be, for example, random copolymers, alternating copolymers, block copolymers or graft copolymers, and may be, for example, linear, star-shaped, or branched (e.g., dendritic copolymers including arborescent copolymers).

A "maleic anhydride graft polymer" is a polymer (e.g., a homopolymer or copolymer) onto which maleic anhydride groups or derivatives of maleic anhydride groups (for example, the free acid, salt, or partial ester form of maleic anhydride) are grafted. Examples of polymers onto which maleic anhydride groups or derivatives of the same can be grafted are found within the list of blending/crosslinking polymers provided below.

Examples of maleic anhydride copolymers for the practice of the present invention include copolymers of (1) a monomer of maleic anhydride or a derivative of the same (which may be, for example, in any of the above forms, including the anhydride, free acid, acid salt, and partial ester forms) with (2) at least one additional monomer, commonly selected from unsaturated monomers such as: (a) alkylene monomers, such as ethylene, propylene, butylenes (e.g., butylene, isobutylene), isoprene, octadecenes (e.g., 1-octadecene) and cyclic alkylenes; (b) halogenated alkylene monomers (e.g., tetrafluoroethylene and chloroethylene); (c) vinyl monomers and derivatives, such as methyl vinyl ether, vinyl acetate, vinyl ethylene (butadiene), vinyl chloride, vinyl pyrrolidone, vinyl cyanide (acrylonitrile), vinyl alcohol, and vinyl aromatics (e.g., styrene and styrene derivatives such as alpha-methyl styrene, ring-alkylated styrenes or ring-halogenated styrenes, or other substituted styrenes where one or more substituents are present on the aromatic ring); and (d) acrylic acid monomers and derivatives, such as methyl acrylate, methyl methacrylate, acrylic acid, methacrylic acid, hydroxyethyl acrylate, hydroxyethyl methacrylate, glyceryl acrylate, glyceryl methacrylate, acrylamide, methacrylamide and ethacrylamide.

More preferred copolymers include styrene maleic anhydride copolymers, including copolymers of styrene and maleic anhydride derivatives (e.g., a copolymer of styrene and the partial methyl ester of maleic anhydride), isobutylene maleic anhydride copolymers, methyl vinyl ether maleic anhydride copolymers, ethylene maleic anhydride copolymers, vinyl acetate maleic anhydride copolymers, octadecene maleic anhydride copolymers, and butadiene maleic anhydride copolymers. Examples of maleic anhydride graft polymers include olefin polymers and copolymers grafted with maleic anhydride, including polymers and copolymers of polyethylene, polypropylene, polybutylene, polybutadiene, etc., grafted with maleic anhydride. A specific example is Kraton™ FG-1901X, a styrene/(butadiene/butylene)/styrene tri-block copolymer (SEBS) grafted with about 2 wt % maleic anhydride available from Kraton Polymers.

In forming the release layers of the present invention, the above maleic anhydride copolymers and graft polymers can be blended or crosslinked with one or more additional polymers (referred to herein as "blending/crosslinking polymers"), if desired. The additional polymers can be added, for example, to influence the strength or diffusion properties of the release layer. The additional polymers may be, for example, homopolymers or copolymers, crosslinked or uncrosslinked, linear or branched, natural or synthetic, thermoplastic or thermosetting.

Blending/crosslinking polymers include the following: polycarboxylic acid polymers and copolymers including polyacrylic acids (e.g., acrylic latex dispersions and various polyacrylic acid products such as HYDROPLUS, available from Boston Scientific Corporation, Natick Mass. and described in U.S. Pat. No. 5,091,205, the disclosure of which is hereby incorporated herein by reference, and HYDROPASS, also available from Boston Scientific Corporation); acetal polymers and copolymers; acrylate and methacrylate polymers and copolymers; cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydoxyalkyl celluloses; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, polystyrenes, styrene-butadiene copolymers, acrylonitrile-styrene copolymers, acrylonitrile-butadiene-styrene copolymers, styrene-butadiene-styrene copolymers and styrene-isobutylene-styrene copolymers, polyvinyl ketones, polyvinylcarbazoles, and polyvinyl esters such as polyvinyl acetates; polybenzimidazoles; ionomers; polyalkyl oxide polymers and copolymers including polyethylene oxides (PEO); glycosaminoglycans; polyesters including polyethylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates (e.g., U.S. Pat. No. 5,091,205 describes medical devices coated with one or more polyisocyanates such that the devices become instantly lubricious when exposed to body fluids); polyolefin polymers and copolymers, including polyalkylenes such as polypropylenes, polyethylenes (low and high density, low and high molecular weight), polybutylenes (such as polybut-1-ene and polyisobutylene), poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; polyurethanes (e.g., BAYHYDROL polyurethane dispersions); p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as blends and copolymers of the above.

Some exemplary additional blending/crosslinking polymers for use in combination with the present invention are block copolymers comprising at least two polymeric blocks A and B. Examples of such block copolymers include the following: (a) BA (linear diblock), (b) BAB or ABA (linear triblock), (c) B(AB)$_n$ or A(BA)$_n$ (linear alternating block), or (d) X-(AB)$_n$ or X-(BA)$_n$ (includes diblock, triblock and other radial block copolymers), where n is a positive whole number and X is a starting seed, or initiator, molecule.

One specifically preferred group of polymers have X-(AB)$_n$ structures, which are frequently referred to as diblock copolymers and triblock copolymers where n=1 and n=2, respectively (this terminology disregards the presence of the starting seed molecule, for example, treating A-X-A as a single A block with the triblock therefore denoted as BAB). Where n=3 or more, these structures are commonly referred to as star-shaped block copolymers.

Other examples of additional polymers include branched block copolymers such as dendritic block copolymers (e.g., arborescent block copolymers), wherein at least one of the A and B blocks is branched, and preferably wherein the A blocks are branched and capped by the B blocks.

The A blocks are preferably soft elastomeric components which are based upon one or more polyolefins or other polymer with a glass transition temperature at or below room temperature. For example, the A blocks can be polyolefinic blocks having alternating quaternary and secondary carbons of the general formulation: —(CRR'—CH$_2$)$_n$—, where R and R' are linear or branched aliphatic groups such as methyl, ethyl, propyl, isopropyl, butyl, isobutyl and so forth, or cyclic aliphatic groups such as cyclohexane, cyclopentane, and the like, with and without pendant groups. Preferred polyolefinic blocks include blocks of isobutylene, (i.e., polymers where R and R' are the same and are methyl groups). Other examples of A blocks include silicone rubber blocks and acrylate rubber blocks.

The B blocks are preferably hard thermoplastic blocks with glass transition temperatures significantly higher than the elastomeric A block that, when combined with the soft A blocks, are capable of, inter alia, altering or adjusting the hardness of the resulting copolymer to achieve a desired combination of qualities. Preferred B blocks are polymers of methacrylates or polymers of vinyl aromatics. More preferred B blocks are (a) made from monomers of styrene styrene derivatives (e.g., α-methylstyrene, ring-alkylated styrenes or ring-halogenated styrenes or other substituted styrenes where one or more substituents are present on the aromatic ring) or mixtures of the same, collectively referred to herein as "styrenic blocks" or "polystyrenic blocks" or are (b) made from monomers of methylmethacrylate, ethylmethacrylate hydroxyethyl methacrylate or mixtures of the same.

More preferred are blending/crosslinking polymers that are elastomeric. As defined herein, an "elastomeric" polymer is a polymer that can be stretched to at least 1.5 times its original length at room temperature and, upon release of the stretching stress, will return with force to its approximate original length.

In some particularly preferred embodiments of the present invention, a maleic anhydride copolymer or graft polymer is combined with one or more of the following elastomers: (a) a copolymer of polyisobutylene with polystyrene or poly-alpha-methylstyrene, more preferably polystyrene-polyisobutylene-polystyrene triblock copolymers which, along with other polymers appropriate for the practice of the present invention, are described, for example, in U.S. Pat. No. 5,741,331, U.S. Pat. No. 4,946,899 and U.S. Ser. No. 09/734,639, each of which is hereby incorporated by reference in its entirety; (b) a copolymer containing one or more blocks of polystyrene and one or more random polymer blocks of ethylene and butylene, for example, a polystyrene-polyethylene/butylene-polystyrene (SEBS) copolymer, available as Kraton™ G series polymers available from Kraton Polymers; (c) a homopolymer of n-butyl methacrylate (BMA); and (d) arborescent polyisobutylene-polystyrene block copolymers such as those described in Kwon et al., "Arborescent Polyisobutylene-Polystyrene Block Copolymers-a New Class of Thermoplastic Elastomers," *Polymer Preprints*, 2002, 43(1), 266, which is hereby incorporated by reference in its entirety.

Where crosslinking of two polymers (sometimes also referred to as polymer grafting or polymer coupling) is desired, the maleic anhydride groups (and derivatives thereof) that are present on the maleic anhydride copolymers and graft polymers of the present invention can take part in the reaction. As one specific example, an available maleic anhydride group (e.g., a maleic anhydride group on a maleic anhydride copolymer or graft polymer) can be reacted with an amino alcohol according to the following scheme (where "polymer" designates a preselected polymer moiety).

A thus-functionalized maleic anhydride copolymer or graft polymer can subsequently be reacted with a variety of polymers, including additional maleic anhydride copolymers according to the following scheme:

A specific example corresponding to the above sequence is the case where an amino alcohol is used to crosslink (a) a styrene/(butadiene/butylene)/styrene tri-block copolymer having grafted maleic acid end groups (e.g., Kraton™ FG-1901X, described above) with (b) maleic anhydride groups within a styrene maleic anhydride copolymer.

For further information concerning a crosslinking reaction of this nature, see, e.g., Perez-Camacho, O. Gonzalez-Roa, C. Navarro-Rodriguez, D. Contreras, D Zaragoza. "Preparation of hydroxyl-functionalized SEBS for in situ graft reaction compatibilizing agents." *Journal of Applied Polymer Science*. Vol. 64, No. 13, Jun. 27, 1997, pp. 2519-2528, the entire disclosure of which is incorporated by reference.

Although the first step in the above reaction sequence utilizes a polymer with a maleic anhydride end group, while the second step utilizes a polymer with an internal maleic anhydride group, various other combinations of end groups and internal groups are possible for this reaction sequence.

Indeed, innumerable other crosslinking reactions, including crosslinking reactions that do not rely on the presence of maleic anhydride groups, are known in the art for crosslinking a wide range of polymers such as those listed above.

The release characteristics associated with the release layers of the present invention can be varied in a number of ways in accordance, including the following: (a) varying the type of maleic anhydride copolymer(s) and/or maleic anhydride graft polymer(s) used within the release layer, (b) varying the molecular weight of the maleic anhydride copolymer(s) and/or maleic anhydride graft polymer(s) used within the release layer, (c) varying the relative amount of maleic anhydride monomer in the copolymer, relative to the other monomers, (d) providing one or more blending/crosslinking polymers within the release layer in addition to the maleic anhydride copolymer(s) and/or graft polymer(s), and (e) varying the type, molecular weight and/or relative amount of the blending/crosslinking polymers. Several of these effects are demonstrated in the Examples below.

Medical devices having an extended release profile are preferred in many cases. By "sustained release profile" is meant a release profile in which less than 25% of the total release from the medical device that occurs over the course of implantation/insertion in the body occurs within the first 1-3 days of administration. Conversely, this means that more than 75% of the total release from the medical device will occur after the device has been implanted/inserted for 1-3 days.

In general, the release layers of the present invention are formed using any number of known techniques. Solvent-based techniques, in which the polymer is dissolved or dispersed in a solvent prior to layer formation, are preferred.

Where solvent-based techniques are used, the solvent system that is selected will contain one or more solvent species. The solvent system preferably is a good solvent for the polymer and, where included, for the therapeutic agent as well. The particular solvent species that make up the solvent system may also be selected based on other characteristics including drying rate and surface tension.

Solvent species that can be used in connection with the present invention include any combination of one or more of the following: (a) water, (b) alkanes such as ethane, hexane, octane, cyclohexane, heptane, isohexane, butane, pentane, isopentane, 2,2,4-trimethlypentane, nonane, decane, dodecane, hexadecane, eicosane, methylcyclohexane, cis-decahydronaphthalene and trans-decahydronaphthalene, (c) aromatic species such as benzene, toluene, xylene(s), naphthalene, styrene, ethylbenzene, 1-methylnaphthalene, 1,3,5-trimethylbenzene, tetrahydronaphthalene, diphenyl and 1,4-diethylbenzene, (d) halohydrocarbons including (i) chlorohyhdrocarbons such as chloroform, methyl chloride, dichloromethane, 1,1-dichloroethylene, ethylene dichloride, ethylidene chloride, propyl chloride, cyclohexyl chloride, 1,1,1-trichloroethane, perchloroethylene, trichloroethylene, butyl chloride, carbon tetrachloride, tetrachloroethylene, chlorobenzene, o-dichlorobenzene, benzyl chloride, trichlorobiphenyl, methylcyclohexane, 1,1,2,2-tetrachloroethane (ii) fluorinated halogenated species such as chlorodiflouoromethane, dichlorofluoromethane, dichlorodifluoromethane, trichlorofluoromethane, 1,2-dichlorotetrafluoroethane, 1,1,2-trichlorotrifluoroethane, perfluor (methylcyclohexane), perfluor(dimethylcyclohexane) and (iii) other halohydrocarbons such as ethyl bromide, ethylidene bromide, ethylene dibromide, tribromomethane, bromotrifluoromethane, 1,1,2,2-tetrabromoethane, bromobenzene, bromochloromethane, 1-bromonaphthalene, methyl iodide, methylene diiodide (e) acid aldehydes/anhydrides such as acetaldehyde, furfural, butyraldehyde, benzaldehyde, acetyl chloride, succinic anhydride and acetic anhydride, (f) alcohols including (i) phenols such as phenol, 1,3-benzenediol, m-cresol, o-methoxyphenol, methyl salicylate and nonylphenol, (ii) polyhydric alcohols such as ethylene glycol, glycerol, propylene glycol, 1,3-butanediol, diethylene glycol, triethylene glycol, hexylene glycol and dipropylene glycol, and (iii) other alcohols such as methanol, ethanol, ethylene cyanohydrin, allyl alcohol, 1-propanol, 2-propanol, 3-chloropropanol, furfuryl alcohol, 1-butanol, 2-butanol, benzyl alcohol, isobutanol, cyclohexanol, 1-pentanol, 2-ethyl-1-butanol, diacetone alcohol, 1,3-dimethyl-1-butanol, ethyl lactate, butyl lactate, ethylene glycol monomethyl ether, ethylene glycol monoethyl ether, diethylene glycol monomethyl ether, diethylene glycol monoethyl ether, ethylene glycol monobutyl ether, 2-ethyl-1-hexanol, 1-octanol, 2-octanol, diethylene glycol monobutyl ether, 1-decanol, 1-tridecyl alcohol, nonyl-phenoxy ethanol, oleyl alcohol, triethylene glycol mono-oleyl ether, (g) ethers such as, epichlorohydrin, furan, 1,4-dioxane, dimethoxymethane, diethyl ether, bis-(2-chloroethyl) ether, anisole, di-(2-methoxyethyl) ether, dibenzyl ether, di-(2-chloroisopropyl) ether, bis-(m-phenoxyphenol) ether, dimethyl ether and tetrahydrofuran, (h) ketones, such as acetone, cylohexanone, isophorone, diethyl ketone, mesityl oxide, acetophenone, methyl ethyl ketone, methyl isoamyl ketone, methyl isobutyl ketone, and methyl propyl ketone, (i) acids such as formic acid, acetic acid, benzoic acid, butyric acid, octanoic acid, oleic acid, stearic acid, (j) esters/acetates such as ethylene carbonate, butyrolactone, propylene-1,2-carbonate, ethyl chloroformate, ethyl acetate, trimethyl phosphate, diethyl carbonate, diethyl sulfate, ethyl formate, methyl acetate, n-butyl acetate, isobutyl acetate, t-butyl acetate, 2-ethoxyethyl acetate, isoamyl acetate, dimethyl phthalate, ethyl cinnamate, triethyl phosphate, diethyl phosphate, butyl benzyl phthalate, dibutyl phthalate, diethyl phthalate, tricrysyl phosphate, tributyl phosphate, dibutyl sebacate, methyl oleate, dioctyl phthalate, dibutyl stearate isopropyl acetate, isobutyl isobutyrate, n-propyl acetate and n-butyl propionate, (k) nitrogen compounds such as acetonitrile, acrylonitrile, propionitrile, butyronitrile, nitromethane, nitroethane, 2-nitropropane, nitrobenzene, ethanolamine, ethylenediamine, 1,1-dimethylhydrazine, 2-pyrrolidone, pyridine, propylamine, morpholine, analine, n-methyl-2-pyrrolidone, butylamine, diethylamine, cyclohexylamine, quinoline, dipropylamine, formamide, n,n-dimethylformamide, n,n-dimethylacetamide, tetramethylurea, hexamethyl phosphoramide, diethylenetriamine, triethylamine and triethanolamine, and (l) sulfur compounds such as carbon disulfide, dimethylsulfoxide, ethanethiol, dimethyl sulfone and diethyl sulfide.

Preferred solvent-based techniques include, but are not limited to, solvent casting techniques, spin coating techniques, web coating techniques, solvent spraying techniques, dipping techniques, techniques involving coating via mechanical suspension, including air suspension, ink jet techniques, electrostatic techniques, and combinations of these processes. Typically, a solution containing solvent and polymer (and, in some cases, a therapeutic agent) is applied to a substrate to form a release layer (e.g., a carrier layer or barrier layer). The substrate is typically all or a portion of an implantable or insertable medical device to which the release layer is applied.

Where appropriate, techniques such as those listed above can be repeated or combined to build up a release layer to a desired thickness. The thickness of the release layer can be varied in other ways as well. For example, in one preferred process, solvent spraying, coating thickness can be increased by modification of coating process parameters, including increasing spray flow rate, slowing the movement between the substrate to be coated and the spray nozzle, providing repeated passes and so forth.

In the case of a carrier layer, for example, a therapeutic agent can be included in the above-described polymer solution if desired, and hence co-established with the carrier layer. In other embodiments, on the other hand, the therapeutic agent can be dissolved or dispersed within a solvent, and the resulting solution contacted with a previously formed polymer layer, for example, using one or more of the solvent based application techniques described above (e.g., dipping, spraying, etc.).

Barrier layers, on the other hand, are formed over a therapeutic-agent-containing region. In some embodiments, however, the therapeutic-agent-containing region comprises one or more polymers, which can be selected, for example, from the polymers listed above. As such, the therapeutic-agent-containing region can also be established using solvent-based techniques (e.g., dipping, spraying, etc.) such as those discussed above. In other embodiments, the therapeutic-agent-containing region beneath the barrier layer is established without an associated polymer. For example, the therapeutic agent can simply be dissolved or dispersed in a liquid, and the resulting solution/dispersion contacted with a substrate, for instance, using one or more of the above-described application techniques.

Where the release layer is formed using a solvent based technique, it is preferably dried after application to remove the solvents. The release layer typically further conforms to the underlying surface during the drying process.

The invention is further described with reference to the following non-limiting Examples.

EXAMPLE 1

A solution is provided that contains 25 weight % tetrahydrofuran (THF), 74 wt % toluene, 0.25 wt % paclitaxel and 0.75 wt % of a polymer composition, which consists of a polystyrene-polyisobutylene-polystyrene block copolymer (SIBS), a random copolymer of styrene and maleic anhydride containing 14-15% wt % maleic anhydride (SMA14), or a blend of these polymers. The SIBS copolymer is synthesized using known techniques such as those described in U.S. Pat. No. 5,741,331, U.S. Pat. No. 4,946,899 and U.S. Ser. No. 09/734,639. The SMA14 copolymer is purchased from Sigma-Aldrich, or is available from Nova Chemical as Dylark 332. All solutions are prepared by (1) mixing the paclitaxel and tetrahydrofuran, (2) adding the copolymer or copolymers, (3) adding the toluene, (4) thoroughly mixing (e.g., overnight), and (5) filtering.

The solution is then placed in a syringe pump and fed to a spray nozzle. A stent is mounted onto a holding device parallel to the nozzle and, if desired, rotated to ensure uniform coverage. Depending on the spray equipment used, either the component or spray nozzle can be moved while spraying such that the nozzle moves along the component while spraying for one or more passes. After a carrier coating is formed in this fashion, the stent is dried, for example, by placing it in a preheated oven for 30 minutes at 65° C., followed by 3 hours at 70° C.

Three stents are formed in this manner for each of the various polymeric solutions. Solutions are made containing the following polymeric constituents: (a) 0.75 wt % SMA14, (b) 0.5 wt % SMA14 and 0.25 wt % SIBS, (c) 0.3 wt % SMA14 and 0.45 wt % SIBS, (d) 0.2 wt % SMA14 and 0.55 wt % SIBS, (e) 0.15 wt % SMA14 and 0.60 wt % SIBS, (f) 0.1 wt % SMA14 and 0.65 wt % SIBS (two data sets), (g) 0.05 wt % SMA14 and 0.7 wt % SIBS, and (h) 0.75 wt % SIBS.

Paclitaxel release is then measured as a function of time in PBS with 0.5% wt % Tween® 20 (polyoxyethylene(20) sorbitan monolaurate) available from Sigma-Aldrich. The results, presented as the cumulative release of paclitaxel as a function of time, are graphically illustrated in FIGS. 1A and 1B.

Figure 1A:
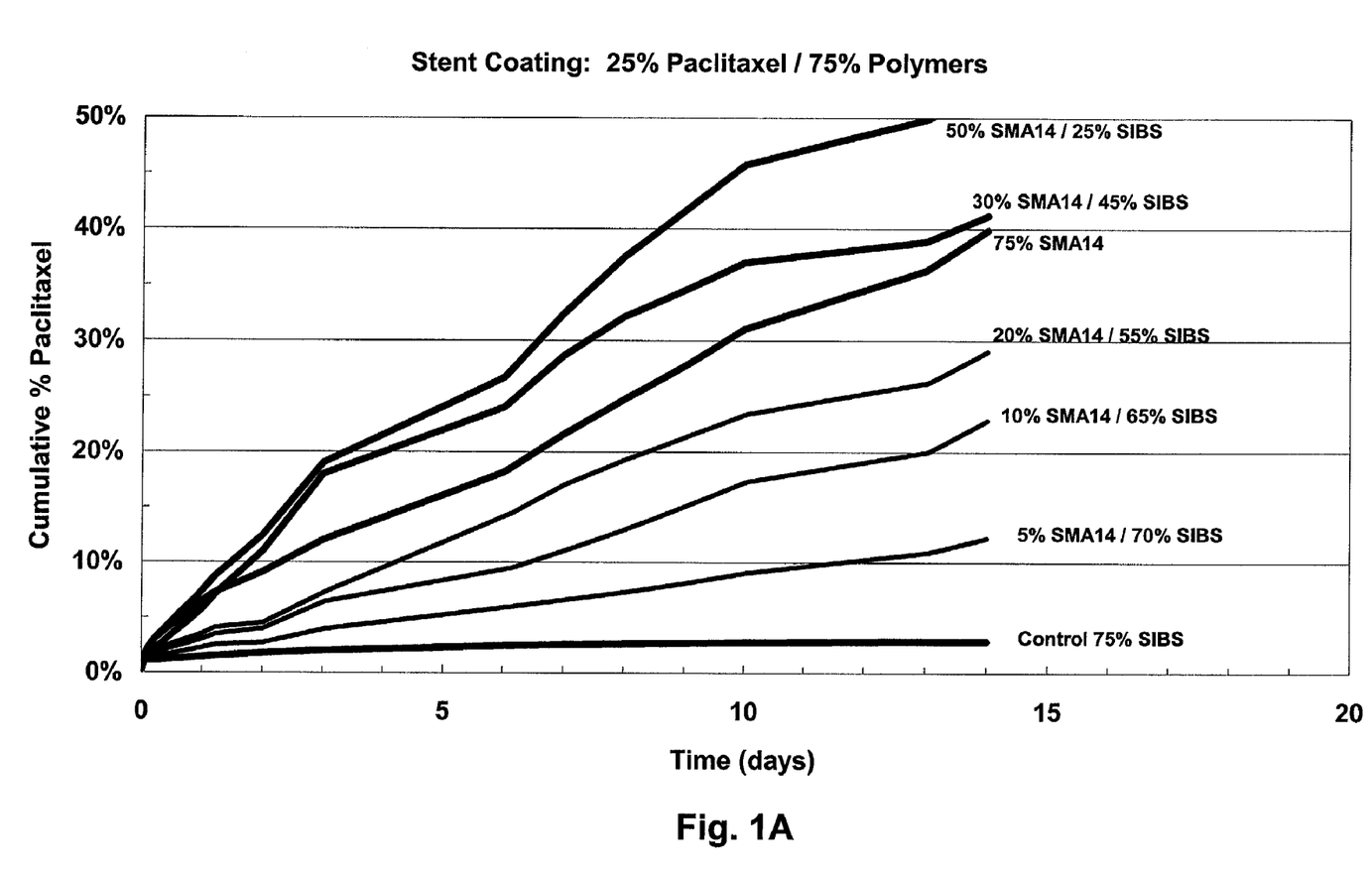
FIGS. 1A and 1B illustrate cumulative release of paclitaxel as a function of time for carrier layers containing paclitaxel and (a) a polystyrene-polyisobutylene-polystyrene block copolymer, (b) a random copolymer of styrene and maleic anhydride, or (c) a polystyrene-polyisobutylene-polystyrene block copolymer blended with a random copolymer of styrene and maleic anhydride, in accordance with an embodiment of the present invention.
Figure 1B:
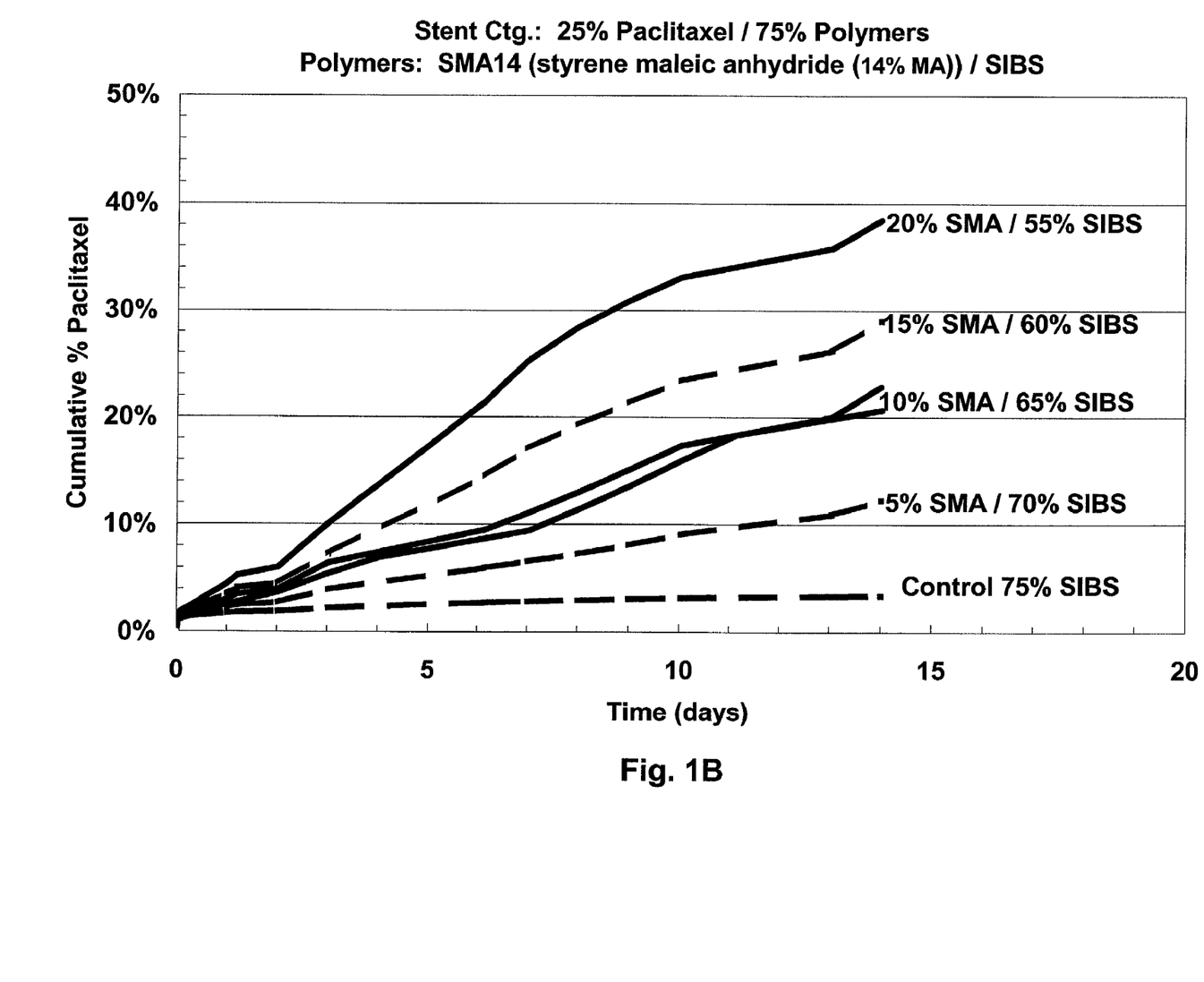

These results indicate that the release rate of a therapeutic agent from a carrier layer comprising a copolymer of maleic anhydride and styrene can be modulated by the addition of a blending polymer in various proportions.

EXAMPLE 2

A series of solutions are prepared in a procedure similar to the procedure used in Example 1. All solutions contain the following: 25 wt % tetrahydrofuran (THF), 74 wt % toluene, 0.25 wt % paclitaxel and 0.75 wt % of a polymer composition.

One control solution is prepared by mixing 0.75 wt % of the homopolymer poly(butyl methacrylate) (BMA) with the solvents and paclitaxel. BMA may be purchased from Sigma-Aldrich at a molecular weight of 337,000.

A first test solution contains 0.65 wt % of the BMA homopolymer and 0.1 wt % of SMA14 copolymer (see Example 1).

A second control solution is prepared with 0.75 wt % of a polystyrene-b-poly(ethylene-r-butylene)-b-polystyrene block copolymer (SEBS). The SEBS copolymer is obtained from Sigma-Aldrich, but is also known by the trade name Kraton™.

A further test solution is prepared using 0.65 wt % of the SEBS copolymer and 0.1 wt % of the SMA14 copolymer.

The solutions are applied to stents and dried according to the procedures of Example 1. Three stents are coated using each of the above solutions. The cumulative release of paclitaxel as a function of time is then measured as in Example 1. The results are graphically illustrated in FIG. 2.

Figure 2:
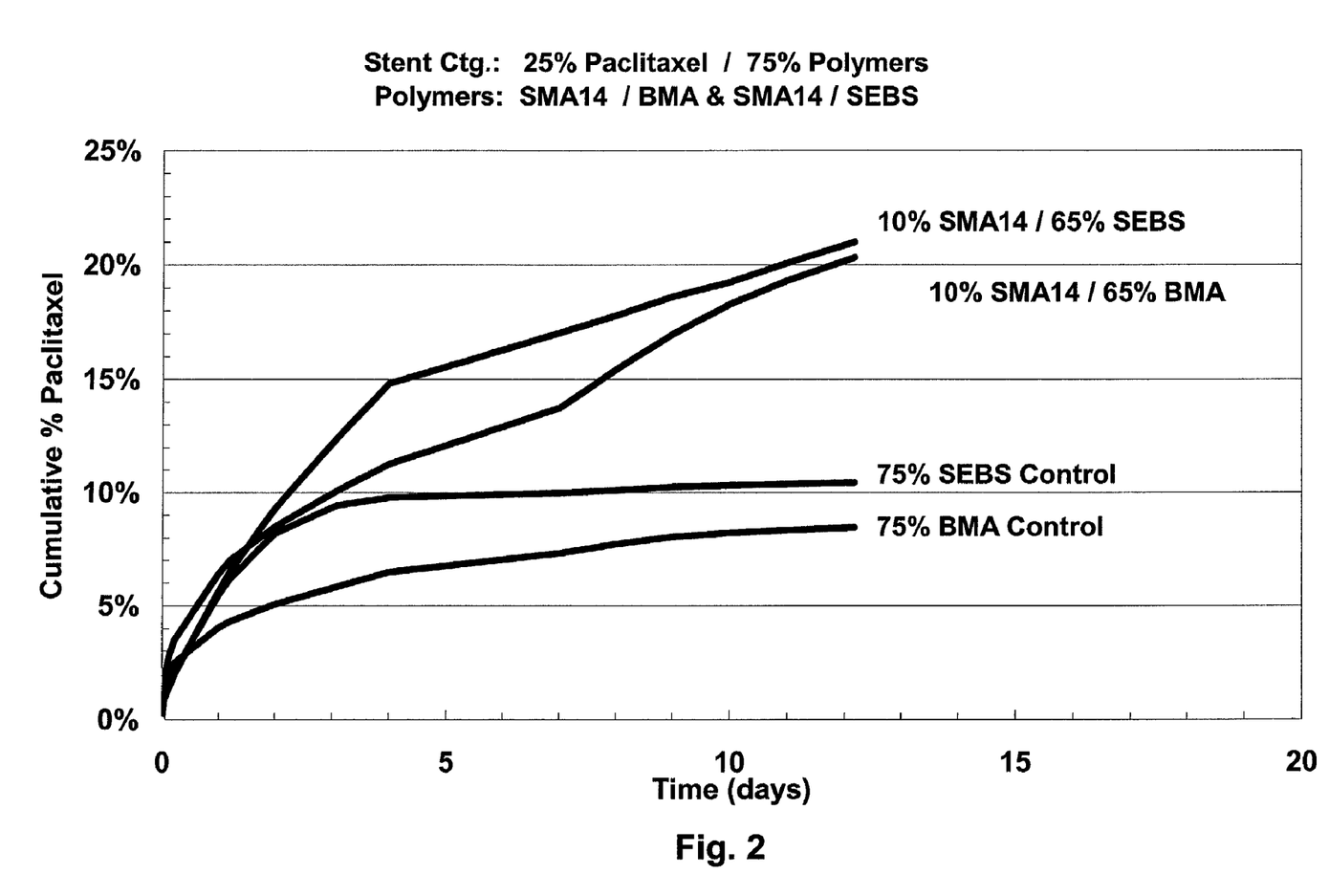
FIG. 2 illustrates cumulative release of paclitaxel as a function of time for carrier layers containing paclitaxel and (a) poly(butyl methacrylate), (b) polystyrene-b-poly(ethylene-r-butylene)-b-polystyrene block copolymer, (c) poly(butyl methacrylate) blended with a random copolymer of styrene and maleic anhydride, and (d) polystyrene-b-poly (ethylene-r-butylene)-b-polystyrene block copolymer blended with a random copolymer of styrene and maleic anhydride.

These results indicate that the release rate of a therapeutic agent from a carrier layer comprising a copolymer of maleic anhydride and styrene can be modulated by the addition various blending polymers.

EXAMPLE 3

A series of solutions are prepared in a procedure like the procedures used in Example 1. All solutions contain the following: 99 wt % solvent system, 0.25 wt % paclitaxel and 0.75 wt % of a polymer composition. The solvent system consists of 25 wt % tetrahydrofuran (THF) and 74 wt % toluene.

A control solution is prepared containing 0.75 wt % SIBS copolymer (see Example 1).

All test solutions contain 0.65 wt % of the SIBS copolymer and 0.1 wt % of a maleic anhydride copolymer.

A first test solution contains 0.1 wt % SMA14 copolymer (see Example 1) and 0.65 wt % of the SIBS copolymer.

A second test solution contains 0.1 wt % of an alternating copolymer of isobutylene and maleic anhydride (IS-a-MA), purchased from Sigma-Aldrich, and 0.65 wt % of the SIBS copolymer.

A third test solution contains 0.1 wt % of an alternating copolymer of methyl vinyl ether and maleic anhydride purchased from Sigma-Aldrich, but also available from ISP Chemical under the trade name of GANTREZ AN, and 0.65 wt % of the SIBS copolymer.

A fourth test solution contains 0.1 wt % of SMA partial ME ester polymer (i.e., styrene maleic anhydride copolymer in which 10-15% of the maleic anhydride groups are reacted to form the methyl ester and carboxyl functional polymer) and 0.65 wt % of the SIBS copolymer.

The solutions are applied to stents and dried according to the procedures of Example 1. Three stents are coated from each of the above solutions. The cumulative release of paclitaxel as a function of time is then measured as in Example 1. The results are graphically illustrated in FIG. 3.

Figure 3:
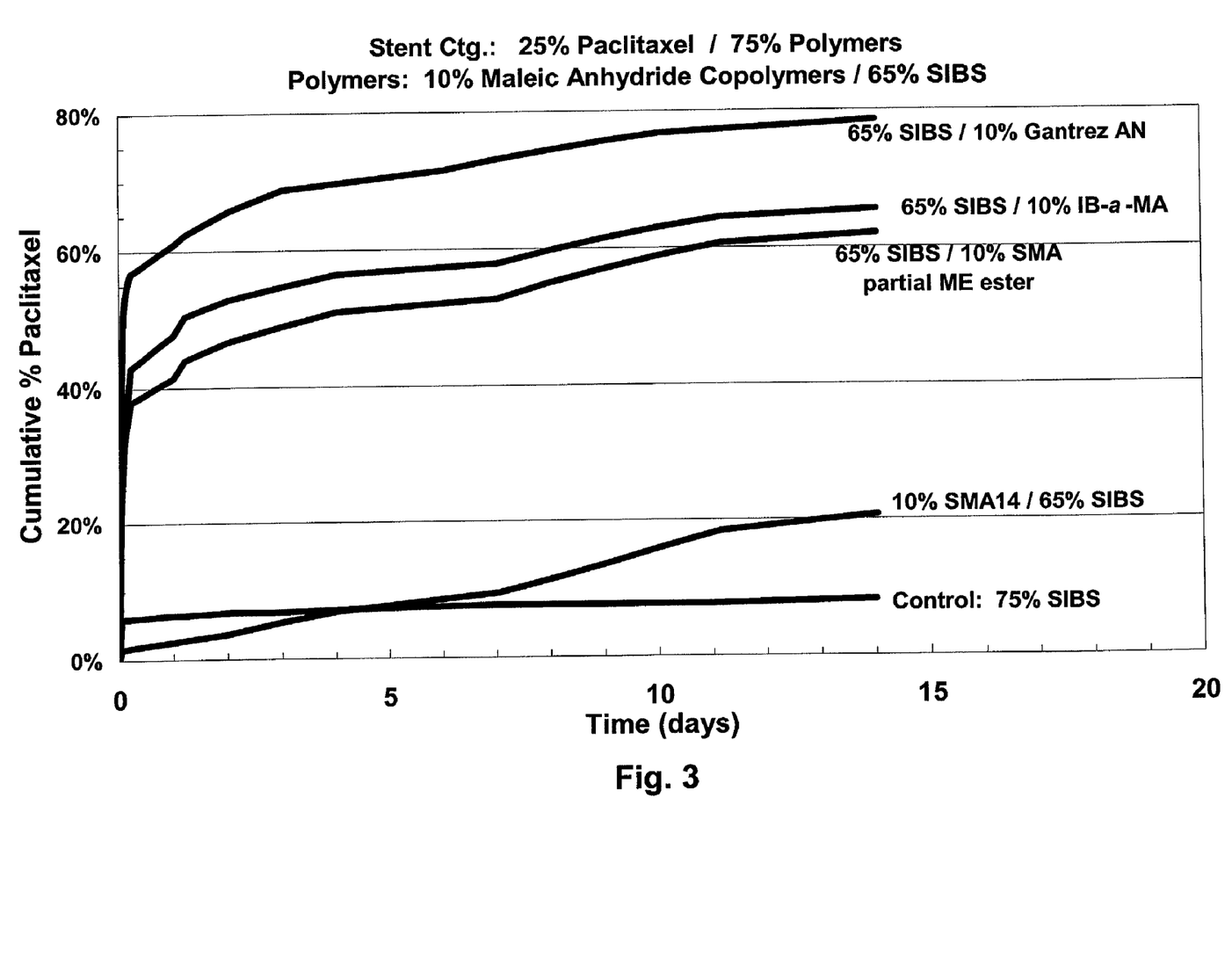
FIG. 3 illustrates cumulative release of paclitaxel as a function of time for carrier layers containing paclitaxel and (a) polystyrene-polyisobutylene-polystyrene block copolymer, (b) polystyrene-polyisobutylene-polystyrene block copolymer blended with a random copolymer of styrene and maleic anhydride, (c) polystyrene-polyisobutylene-polystyrene block copolymer blended with an alternating copolymer of isobutylene and maleic anhydride, (d) polystyrene-polyisobutylene-polystyrene block copolymer blended with an alternating copolymer of methyl vinyl ether and maleic anhydride (e) polystyrene-polyisobutylene-polystyrene block copolymer blended with a styrene maleic anhydride copolymer in which 10-15% of the maleic anhydride groups are reacted to form the methyl ester and carboxyl functional polymer.

These results indicate that a wide variety of maleic anhydride copolymers can be used to modulate the release rate of a therapeutic agent from a carrier layer.

EXAMPLE 4

A series of solutions are prepared in a procedure like that used in Example 1. All solutions contain the following: 25 wt % tetrahydrofuran (THF), 74 wt % toluene, 0.25 wt % paclitaxel and 0.75 wt % polymer.

A control solution is prepared using 0.75 wt % of the SIBS copolymer (see Example 1).

A first test solution is prepared using 0.1% SMA14, a random copolymer of styrene and maleic anhydride containing 14-15 wt % maleic anhydride (see Example 1) and 0.65% SIBS.

A second test solution is prepared using 0.722 wt % SIBS copolymer and 0.028 wt % of an alternating copolymer of styrene and maleic anhydride (SMA50) having a molecular weight of approximately 50,000, purchased from Scientific Polymer Products, Inc.

A third test solution is prepared using 0.722 wt % SIBS copolymer and 0.028 wt % of an alternating copolymer of styrene and maleic anhydride (SMA50) having a molecular weight of approximately 1700, also purchased from Scientific Polymer Products, Inc.

Note that the maleic anhydride (MA) content is the same for all test solutions.

SMA14: 14% MA×10% SMA=1.4% MA total
SMA50: 50% MA×2.8% SMA=1.4% MA total

The solutions are applied to stents and dried according to the procedures of Example 1. Three stents are coated from each of the above solutions. The cumulative release of paclitaxel as a function of time is then measured as in Example 1. The results are graphically illustrated in FIG. 4.

Figure 4:
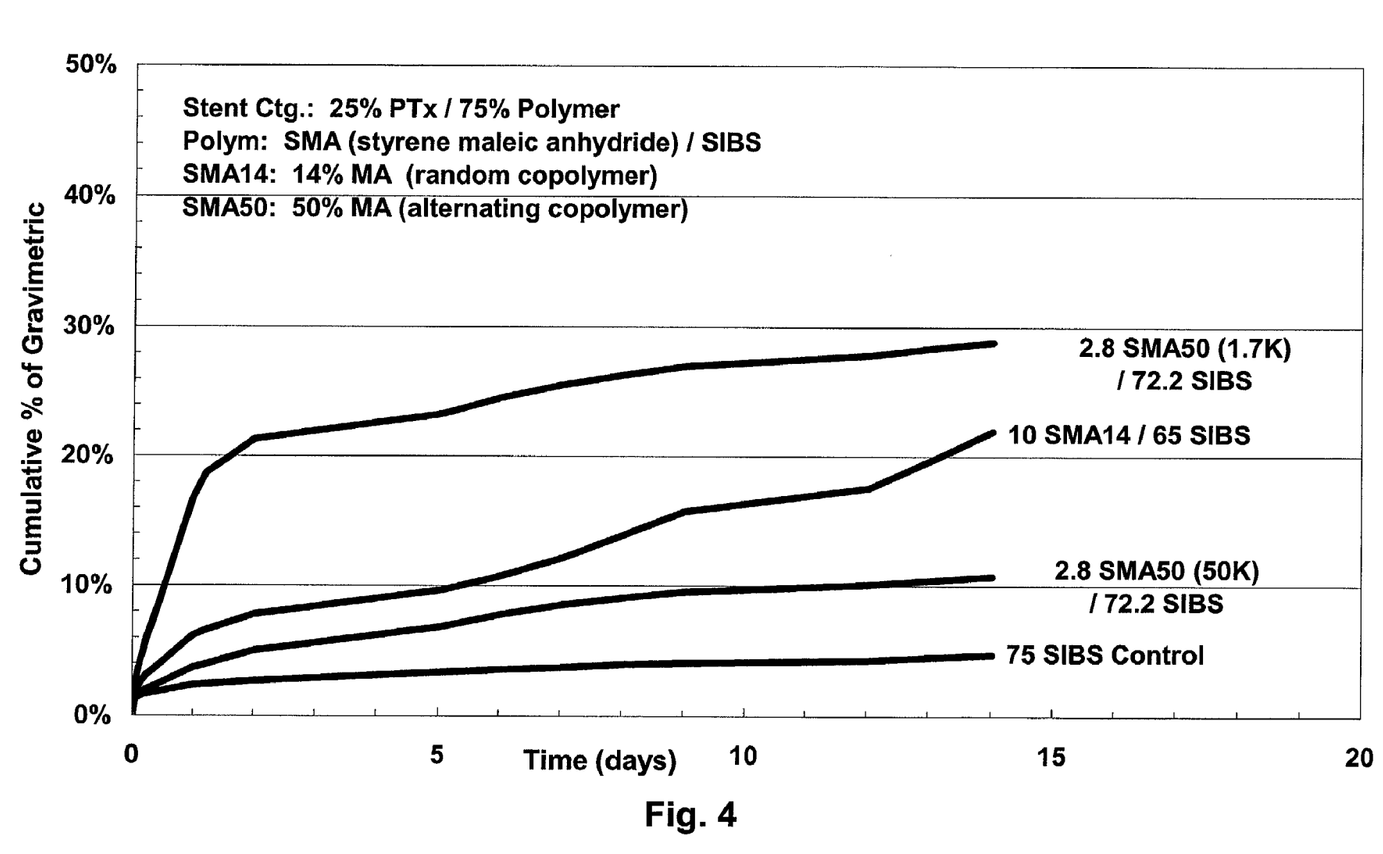
FIG. 4 illustrates cumulative release of paclitaxel as a function of time for carrier layers containing paclitaxel and (a) polystyrene-polyisobutylene-polystyrene block copolymer, (b) polystyrene-polyisobutylene-polystyrene block copolymer blended with a random copolymer of styrene and maleic anhydride, (c) polystyrene-polyisobutylene-polystyrene block copolymer blended with an alternating copolymer of styrene and maleic anhydride having a molecular weight of approximately 50,000, (d) polystyrene-polyisobutylene-polystyrene block copolymer blended with an alternating copolymer of styrene and maleic anhydride having a molecular weight of approximately 1700.

These results indicate that the release rate of a therapeutic agent from a carrier layer containing a copolymer of maleic anhydride and styrene can be modulated by varying the molecular weight of the maleic anhydride copolymer in the carrier layer.

EXAMPLE 5

A solution is provided that contains the following: 5 wt % tetrahydrofuran (THF), 94 wt % toluene, 0.35 wt % paclitaxel and 0.65 wt % SIBS copolymer. The solution is provided by (1) mixing the paclitaxel and tetrahydrofuran, (2) adding the copolymer, (3) adding the toluene, (4) thoroughly mixing (e.g., overnight), and (5) filtering.

The solution is then placed in a syringe pump and fed to a spray nozzle. A stent is mounted onto a holding device parallel to the nozzle and, if desired, rotated to ensure uniform coverage. Depending on the spray equipment used, either the component or spray nozzle can be moved while spraying such that the nozzle moves along the component while spraying for one or more passes. After a coating is formed on the stent in this fashion, it is dried, for example, by placing it in a preheated oven for 30 minutes at 65° C., followed by 3 hours at 70° C.

Three overcoat solutions are prepared containing the following: 25 wt % THF, 74 wt % toluene and 1 wt % of a polymer composition.

A first overcoat solution contains 1 wt % of SIBS copolymer as described above.

A second overcoat solution contains 0.05 wt % of SIBS and 0.05 wt % SMA14 (as described in Example 1).

A third overcoat solution contains 1 wt % SMA14.

Each of the overcoat solutions is individually placed in a syringe pump and fed to a spray nozzle. A coated stent (coated with the SIBS/paclitaxel formulation as described above) is mounted onto a holding device parallel to the nozzle and, if desired, rotated to ensure uniform coverage. Depending on the spray equipment used, either the component or spray nozzle can be moved while spraying such that the nozzle moves along the component while spraying for one or more passes.

Three overcoated stents are formed for each of the three overcoat solutions described above.

After a barrier coating is formed in this fashion, it is dried, for example, by placing it in a preheated oven for 30 minutes at 65° C., followed by 3 hours at 70° C.

The cumulative release of paclitaxel as a function of time is then measured as in Example 1. The results are graphically illustrated in FIG. 5.

Figure 5:
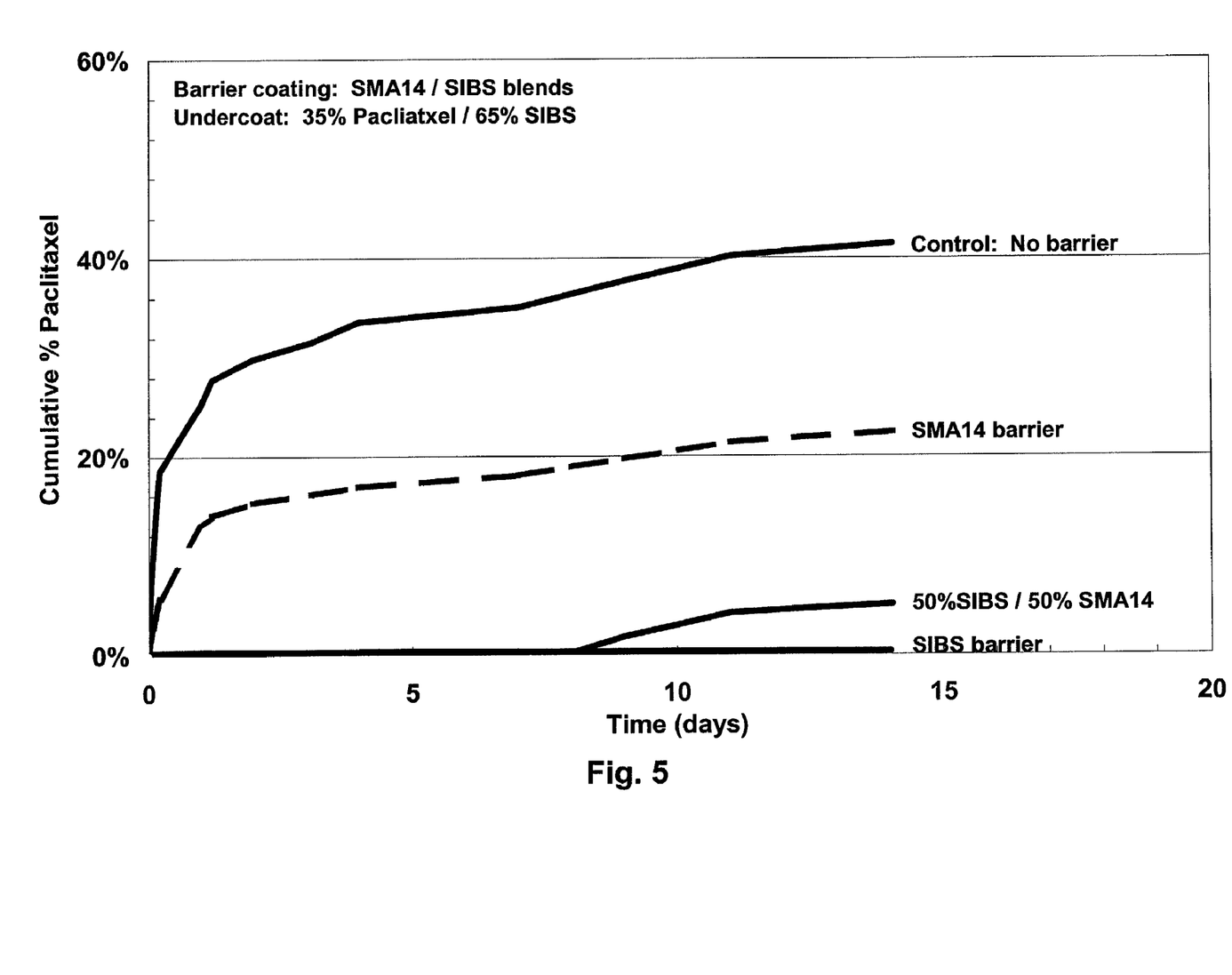
FIG. 5 illustrates cumulative release of paclitaxel as a function of time from barrier layers of (a) a random copolymer of styrene and maleic anhydride or (b) a combination of a random copolymer of styrene and maleic anhydride blended with a polystyrene-polyisobutylene-polystyrene block copolymer, in accordance with another embodiment of the present invention.

These results indicate that the release rate of a therapeutic agent from a therapeutic-agent-containing layer can be modulated using a barrier layer comprising copolymer of maleic anhydride and styrene.

EXAMPLE 6

A series of solutions are prepared in a procedure like that used in Example 1. All solutions contain the following: 25 wt % tetrahydrofuran (THF), 74 wt % toluene, 0.25 wt % paclitaxel and 0.75 wt % polymer.

A control solution is prepared using 0.75 wt % of the SIBS copolymer (see Example 1).

A first test solution is prepared using 0.1% SMA14, a random copolymer of styrene and maleic anhydride containing 14-15 wt % maleic anhydride (see Example 1) and 0.65% SIBS.

A second test solution is prepared using 0.1 wt % SMA7, a random copolymer of styrene and maleic anhydride containing approximately 7 wt % maleic anhydride, and 0.65% SIBS.

The solutions are applied to stents and dried according to the procedures of Example 1. Three stents are coated from each of the above solutions. The cumulative release of paclitaxel as a function of time is then measured as in Example 1. The results are graphically illustrated in FIG. 6.

Figure 6:
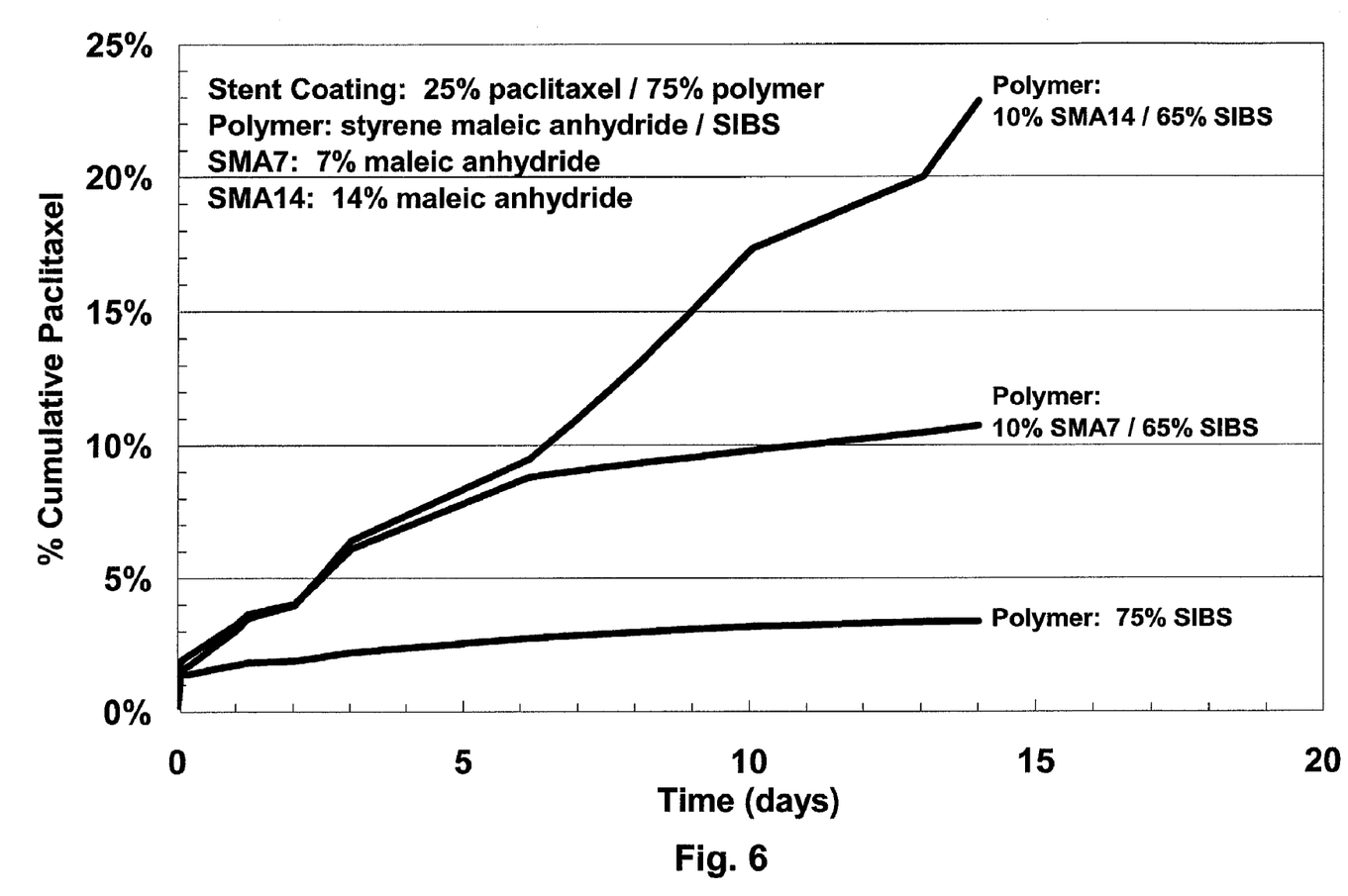
FIG. 6 illustrates cumulative release of paclitaxel as a function of time for carrier layers containing paclitaxel and (a) a polystyrene-polyisobutylene-polystyrene block copolymer, (b) a random copolymer of styrene and maleic anhydride containing approximately 7 wt % maleic anhydride blended with a polystyrene-polyisobutylene-polystyrene block copolymer, and (c) a random copolymer of styrene and maleic anhydride containing approximately 14 wt % maleic anhydride blended with a polystyrene-polyisobutylene-polystyrene block copolymer, in accordance with an embodiment of the present invention.

These results indicate that the release rate of a therapeutic agent from a maleic-anhydride-copolymer-containing carrier layer can be increased by increasing the amount of maleic anhydride monomer relative to the amount of total monomer in a copolymer of maleic anhydride and styrene.

The invention claimed is:

1. A therapeutic-agent-releasing medical device comprising: (a) an implantable or insertable medical device; (b) a therapeutic agent; and (c) a release layer, disposed over at least a portion of the implantable or insertable medical device, that is selected from a carrier layer that comprises said therapeutic agent and a barrier layer that is disposed over a therapeutic-agent-containing region that comprises said therapeutic agent, said release layer comprising (i) a maleic anhydride polymer selected from a maleic anhydride copolymer and a maleic anhydride graft polymer and (ii) an additional polymer selected from poly(butyl methacrylate) and a copolymer that comprises (i) one or more blocks selected from blocks of polyisobutylene and blocks of ethylene and butylene and (ii) one or more polystyrenic blocks, said release layer regulating the rate of release of the therapeutic agent from the medical device upon implantation or insertion of the device into a patient, such that more than 75% of the total release from the medical device that occurs over the course of implantation or insertion in the patient occurs after the device has been inserted for 1 to 3 days.

2. The therapeutic-agent-releasing medical device of claim 1, wherein said medical device comprises said carrier layer.

3. The therapeutic-agent-releasing medical device of claim 1, wherein said medical device comprises said barrier layer.

4. The therapeutic-agent-releasing medical device of claim 1, wherein said implantable or insertable medical device is selected from a catheter, a guide wire, a balloon, a filter, a stent, a stent graft, a vascular graft, a vascular patch, a shunt, and an intraluminal paving system.

5. The therapeutic-agent-releasing medical device of claim 1, wherein said implantable or insertable medical device is adapted for implantation or insertion into the coronary vasculature, peripheral vascular system, esophagus, trachea, colon, biliary tract, urinary tract, prostate or brain.

6. The therapeutic-agent-releasing medical device of claim 1, wherein said therapeutic agent is selected from one or more of the group consisting of an anti-thrombotic agent, an anti-proliferative agent, an anti-inflammatory agent, an anti-migratory agent, an agent affecting extracellular matrix production and organization, an antineoplastic agent, an anti-mitotic agent, an anesthetic agent, an anti-coagulant, a vascular cell growth promoter, a vascular cell growth inhibitor, a cholesterol-lowering agent, a vasodilating agent, and an agent that interferes with endogenous vasoactive mechanisms.

7. The therapeutic-agent-releasing medical device of claim 1, wherein said maleic anhydride polymer is said maleic anhydride copolymer.

8. The therapeutic-agent-releasing medical device of claim 7, wherein said maleic anhydride copolymer is a random copolymer.

9. The therapeutic-agent-releasing medical device of claim 7, wherein said maleic anhydride copolymer is an alternating copolymer.

10. The therapeutic-agent-releasing medical device of claim 7, wherein said maleic anhydride copolymer is a copolymer comprising (a) a monomer comprising a carbon-carbon double bond and (b) a maleic anhydride monomer in a form selected from the anhydride form, free acid form, acid salt form and partial ester form.

11. The therapeutic-agent-releasing medical device of claim 10, wherein said monomer comprising a carbon-carbon double bond is an alkylene monomer.

12. The therapeutic-agent-releasing medical device of claim 11, wherein said alkylene monomer is selected from ethylene, propylene and isobutylene monomers.

13. A therapeutic-agent-releasing medical device comprising: (a) an implantable or insertable medical device; (b) a therapeutic agent; and (c) a release layer, disposed over at least a portion of the implantable or insertable medical device, that is selected from a carrier layer that comprises said therapeutic agent and a barrier layer that is disposed over a therapeutic-agent-containing region that comprises said therapeutic agent, said release layer comprising (i) a maleic anhydride copolymer which is an alternating copolymer of isobutylene and maleic anhydride and (ii) an additional polymer, said release layer regulating the rate of release of the therapeutic agent from the medical device upon implantation or insertion of the device into a patient, such that more than 75% of the total release from the medical device that occurs over the course of implantation or insertion in the patient occurs after the device has been inserted for 1 to 3 days.

14. The therapeutic-agent-releasing medical device of claim 10, wherein said monomer comprising a carbon-carbon double bond is a vinyl monomer.

15. The therapeutic-agent-releasing medical device of claim 14, wherein said vinyl monomer is selected from one or more of vinyl aromatics, vinyl ethers, vinyl acetates, vinyl aliphatics, halogenated vinyl compounds, vinyl pyrrolidones, acrylonitriles, vinyl alcohols, and vinyl acrylamides.

16. The therapeutic-agent-releasing medical device of claim 15, wherein said maleic anhydride copolymer is a random copolymer of styrene and maleic anhydride.

17. The therapeutic-agent-releasing medical device of claim 15, wherein said maleic anhydride copolymer is an alternating copolymer of styrene and maleic anhydride.

18. The therapeutic-agent-releasing medical device of claim 15, wherein said maleic anhydride copolymer is a copolymer of styrene and maleic anhydride, in which a first portion of the maleic anhydride is in the carboxyl or partial ester form and a second portion of the maleic anhydride is in the anhydride form.

19. The therapeutic-agent-releasing medical device of claim 15, wherein said maleic anhydride copolymer is an alternating copolymer of methyl vinyl ether and maleic anhydride.

20. The therapeutic-agent-releasing medical device of claim 1, wherein said release layer comprises said maleic anhydride graft polymer.

21. The therapeutic-agent-releasing medical device of claim 20, wherein said maleic anhydride graft polymer comprises maleic anhydride grafted onto a homopolymer.

22. The therapeutic-agent-releasing medical device of claim 20, wherein said maleic anhydride graft polymer comprises maleic anhydride grafted onto a copolymer.

23. A therapeutic-agent-releasing medical device comprising: (a) an implantable or insertable medical device; (b) a therapeutic agent; and (c) a release layer, disposed over at least a portion of the implantable or insertable medical device, that is selected from a carrier layer that comprises said therapeutic agent and a barrier layer that is disposed over a therapeutic-agent-containing region that comprises said therapeutic agent, said release layer comprising (i) a maleic anhydride copolymer which is a maleic anhydride graft polymer that comprises maleic anhydride grafted onto a copolymer comprising (a) one or more blocks of polystyrene and (b) one or more polymer blocks of ethylene and butylene and (ii) an additional polymer, said release layer regulating the rate of release of the therapeutic agent from the medical device upon implantation or insertion of the device into a patient, such that more than 75% of the total release from the medical device that occurs over the course of implantation or insertion in the patient occurs after the device has been inserted for 1 to 3 days.

24. A therapeutic-agent-releasing medical device comprising: (a) an implantable or insertable medical device; (b) a therapeutic agent; and (c) a release layer, disposed over at least a portion of the implantable or insertable medical device, that is selected from a carrier layer that comprises said therapeutic agent and a barrier layer that is disposed over a therapeutic-agent-containing region that comprises said therapeutic agent, said release layer comprising (i) a maleic anhydride copolymer comprising (a) an isobutylene monomer and (b) a maleic anhydride monomer in a form selected from the anhydride form, free acid form, acid salt form and partial ester form and (ii) an additional polymer that is blended with said maleic anhydride polymer in the release layer, and said release layer regulating the rate of release of the therapeutic agent from the medical device upon implantation or insertion of the device into a patient.

25. The therapeutic-agent-releasing medical device of claim 24, wherein said additional polymer is crosslinked with the maleic anhydride polymer in the release layer.

26. The therapeutic-agent-releasing medical device of claim 24, wherein the additional polymer is a copolymer comprising (a) one or more blocks of polyisobutylene and (b) one or more polystyrenic blocks.

27. The therapeutic-agent-releasing medical device of claim 24, wherein the additional polymer is a copolymer comprising (a) one or more polystyrenic blocks and (b) one or more polymer blocks of ethylene and butylene.

28. The therapeutic-agent-releasing medical device of claim 24, wherein the additional polymer is poly(butyl methacrylate).

29. The therapeutic-agent-releasing medical device of claim 25, wherein the additional polymer is a copolymer comprising (a) one or more polystyrenic blocks and (b) one or more polymer blocks of ethylene and butylene.

30. A method of forming the therapeutic-agent-releasing medical device of claim 1, comprising: (a) providing a solution comprising one or more solvents and said maleic anhydride polymer; (b) applying said solution to a surface of said implantable or insertable medical device; and (c) removing said solvents from said solution to form said release layer.

31. The method of claim 30, wherein said solution further comprises said therapeutic agent.

32. The method of claim 30, wherein said solution is applied over said therapeutic-agent-containing region that comprises said therapeutic agent.

33. The method of claim 30, wherein said solution is applied by a solvent spraying technique.

34. The method of claim 30, wherein said solution comprises a maleic anhydride copolymer.

35. The method of claim 30, wherein said solution comprises a maleic anhydride graft polymer.

36. The method of claim 30, wherein said solution further comprises an additional polymer.

37. A method of releasing a therapeutic agent within a patient comprising (a) providing the therapeutic-agent-releasing medical device of claim 1 and (b) implanting or inserting the therapeutic-agent-releasing medical device into a patient.

38. The method of claim 37, wherein said medical device is selected from a catheter, a guide wire, a balloon, a filter, a stent, a stent graft, a vascular graft, a vascular patch, a shunt, and an intraluminal paving system.

39. The method of claim 37, wherein said medical device is inserted into the vasculature.

40. The method of claim 39, wherein said therapeutic agent is released in the treatment of restenosis.

41. The therapeutic-agent-releasing medical device of claim 24, wherein the additional polymer is a copolymer comprising (a) one or more polyolefinic blocks and (b) one or more polystyrenic blocks.

42. A therapeutic-agent-releasing medical device comprising:
an implantable or insertable medical device;
a release layer disposed over at least a portion of the implantable or insertable medical device, said release layer comprising (a) a maleic anhydride copolymer that comprises (i) a monomer selected from styrene, isobutylene and methyl vinyl ether and (ii) a maleic anhydride monomer in a form selected from the anhydride form, free acid form, acid salt form and partial ester form and (b) an additional copolymer that comprises (i) one or more blocks selected from blocks of polyisobutylene and blocks of ethylene and butylene and (ii) one or more polystyrenic blocks; and
a therapeutic agent,
said release layer regulating the rate of release of the therapeutic agent from the medical device upon implantation or insertion of the device into a patient.

43. The therapeutic-agent-releasing medical device of claim 1, wherein more than 75% of the total release from the medical device that occurs over the course of implantation or insertion in the patient occurs after the device has been inserted for a period of 1 day.

44. The therapeutic-agent-releasing medical device of claim 1, wherein more than 75% of the total release from the medical device that occurs over the course of implantation or insertion in the patient occurs after the device has been inserted for a period of 3 days.

* * * * *